(12) United States Patent
Thramann

(10) Patent No.: US 6,602,257 B1
(45) Date of Patent: Aug. 5, 2003

(54) CERVICAL PLATE

(76) Inventor: Jeffrey J. Thramann, 8519 Strawberry La., Niwot, CO (US) 80544

( * ) Notice: Subject to any disclaimer, the term of this patent is extended or adjusted under 35 U.S.C. 154(b) by 0 days.

(21) Appl. No.: 10/178,371

(22) Filed: Jun. 24, 2002

(51) Int. Cl.[7] .............................................. A61B 17/58
(52) U.S. Cl. ............................ 606/69; 606/61; 606/70
(58) Field of Search ............................ 606/69, 70, 71, 606/72, 96, 99, 101

(56) References Cited

U.S. PATENT DOCUMENTS 5,957,927 A * 9/1999 Magee et al. ................. 606/99
6,159,213 A * 12/2000 Rogozinski .................. 606/70
6,224,599 B1 * 5/2001 Baynham et al. ............. 606/61
6,436,101 B1 * 8/2002 Hamada ....................... 606/85

* cited by examiner

*Primary Examiner*—Cary E. O'Connor
*Assistant Examiner*—Candice C. Melson
(74) *Attorney, Agent, or Firm*—Holland & Hart

(57) ABSTRACT

The present invention provides a cervical plate and bone graft(s) that are capable of being attached prior to insertion of the bone graft into an intervertebral space. After insertion, the vertebrae hold the bone graft and cervical plate in place facilitating the anchoring of the cervical plate to the vertebrae.

42 Claims, 5 Drawing Sheets

CERVICAL PLATE

CERVICAL PLATE

This application is related to an application filed concurrently herewith entitled IMPACTOR FOR USE WITH CERVICAL PLATE, by Jeffrey J. Thramann, M.D.

FIELD OF THE INVENTION

The present invention relates to apparatuses and methods for treating and correcting spinal abnormalities and, more particularly, to cervical plates useful in procedures relating to the insertion of bone grafts in the spine and fusing vertebrae.

BACKGROUND OF THE INVENTION

The vertebrae of the human spine are arranged in a column with one vertebra on top of the next. Between each vertebra exists an intervertebral disc that transmits force between adjacent vertebrae and provides a cushion between the adjacent vertebrae.

Sometimes, back pain is caused by degeneration or other deformity of the intervertebral disc ("diseased disc"). When a diseased disc impinges upon neurological structures or is determined to be a pain generator, surgeons treat the diseased disc by surgically removing the diseased disc and inserting a bone graft in the space vacated by the diseased disc. The adjacent vertebrae are then immobilized relative to one another with a cervical plate and screws. Eventually, the vertebrae grow into one solid piece of bone.

Currently, it can be difficult to insert the bone graft into the vacated space and fuse the adjacent vertebrae. The current process of inserting a bone graft and fusing the adjacent vertebrae will be explained referring to FIGS. 1 and 2. FIG. 1 shows two adjacent vertebrae 102 and 104. Located between vertebrae 102 and 104 is an intervertebral space 106 partially filled by a bone graft 108. When the bone graft 108 is first inserted into the intervertebral space 106, the adjacent vertebrae 102 and 104 are manually kept apart by the surgeon using, for example, a retracting device (not shown). As shown in FIG. 2, once the bone graft 108 is placed, the surgeon releases the adjacent vertebrae 102 and 104 allowing them to squeeze the bone graft 108 and hold the bone graft 108 in place.

To immobilize the vertebrae 102 and 104 with the bone graft 108 in place, the surgeon next applies a cervical plate 202 over the adjacent vertebrae 102 and 104. Cervical plate 202 may have a central viewing window 204 and one or more screw holes 206, in this example four screw holes 206a–206d are shown. Four bone screws, which are identified by reference numerals 208a–208d, and shown in screw holes 206a–206d respectively, would be screwed into the vertebrae using the screw holes 206 to anchor the cervical plate to the vertebrae and immobilize the vertebrae with respect to one another.

As can be appreciated, attaching the cervical plate 202 using the bone screws 208 can be a difficult endeavor. Generally, a temporary screw (also not shown) is placed in one of the screw holes, for example 206a. Bone screw 208c would then be partially screwed into the bone at screw hole 206c. The temporary screw in hole 206a would be replaced by bone screw 208a, which would be tightened. Then the other bone screws 208 would be screwed into the bone in a cross point manner. The ability of the cervical plate to move freely in relation to the vertebrae 102 and 104 and the bone graft 108 until the bone screws anchor the plate causes difficulty in attaching the cervical plate. This is made more difficult because, generally, only a portion of the cervical plate is visible to the surgeon at any given moment (due to space constraints and surgical tools).

While the above example relates to replacement of one intervertebral disc between two adjacent vertebrae, sometimes it is necessary to replace two or more discs spanning three or more vertebrae. The problems associated with replacing one disc become more exacerbated the more discs and vertebrae that are involved.

Due to the small margins for error in placing the bone screws into the vertebrae, it would be desirous to develop a cervical plate that was not as free to move prior to attachment with the bone screws, and one that automatically aligned the screw holes over the adjacent vertebral bodies.

SUMMARY OF THE INVENTION

The foregoing and other features, utilities and advantages of the invention will be apparent from the following more particular description of a preferred embodiment of the invention as illustrated in the accompanying drawings. Further, the advantages and purpose of the invention will be realized and attained by means of the elements and combinations particularly pointed out in the appended claims.

To attain the advantages and in accordance with the purpose of the invention, as embodied and broadly described herein, apparatuses to facilitate the insertion of a bone graft into an intervertebral space and positioning of a cervical plate are provided. In particular, a cervical plate having an attachment mechanism that allows a surgeon to attach the bone graft to the cervical plate is provided. The bone graft, when inserted into the intervertebral space, holds the cervical plate in position to facilitate the anchoring of the cervical plate to vertebrae, and by taking advantage of the fixed association of the junction of the graft and the vertebral endplate with the cervical plate, ensures the screw holes of the cervical plate are optimally placed over the adjacent vertebral bodies to further facilitate screw placement for anchoring of the cervical plate to vertebrae.

The present invention further provides an impactor. The impactor is releasably coupled to the cervical plate and has a handle and prongs. The prongs assist in separating the vertebrae to facilitate the insertion of the bone graft, which is attached to the cervical plate via an attachment mechanism, into the intervertebral space.

The present invention still further provides methods for correcting abnormalities of the spine by inserting bone grafts.

BRIEF DESCRIPTION OF THE DRAWING

The accompanying drawings, which are incorporated in and constitute a part of this specification, illustrate embodiments of the present invention, and together with the description, serve to explain the principles thereof. Like items in the drawings are referred to using the same numerical reference.

DETAILED DESCRIPTION

Figure 1:
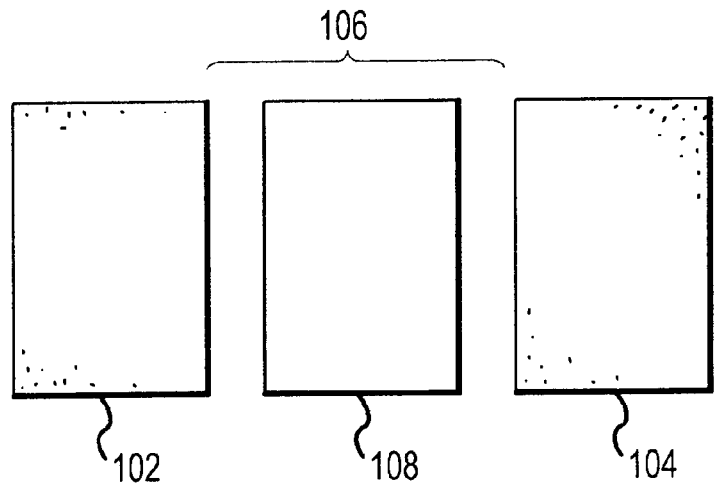
FIG. 1 shows adjacent vertebrae with a bone graft.
Figure 2:
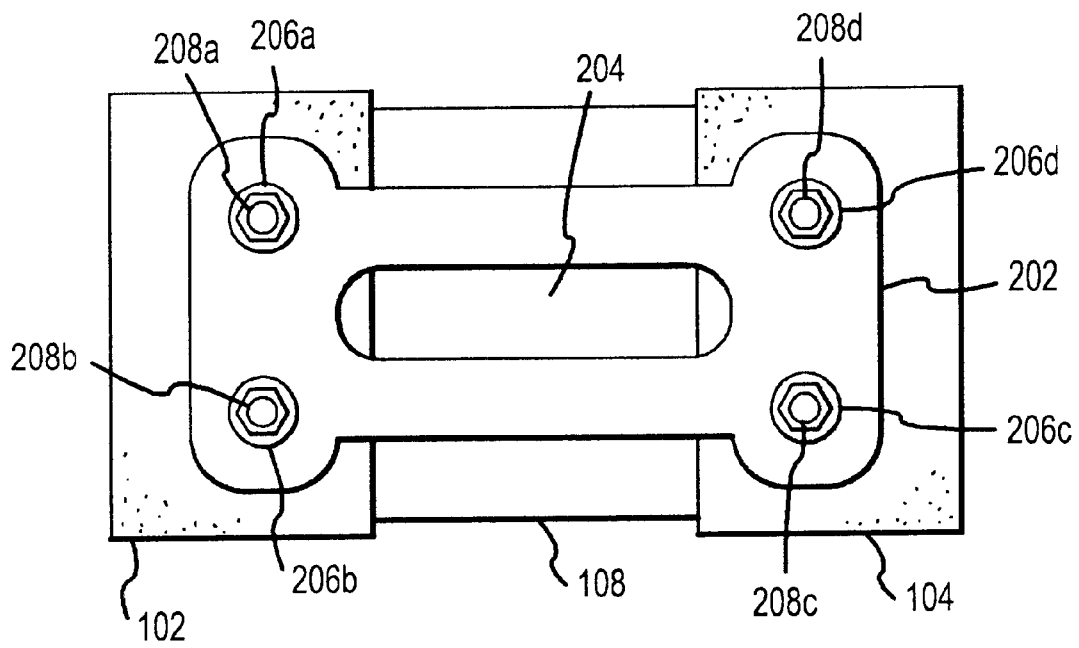
FIG. 2 shows adjacent vertebrae with a bone graft and cervical plate.
Figure 3:
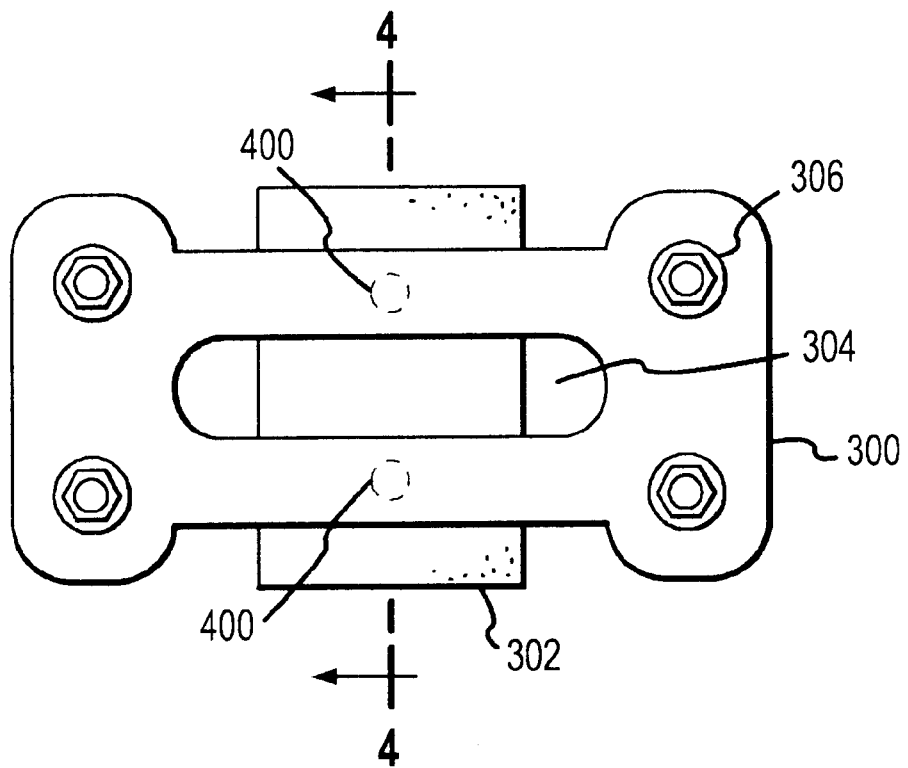
FIG. 3 shows adjacent vertebrae with a bone graft and cervical plate having an attachment mechanism illustrative of the present invention.
Figure 4:
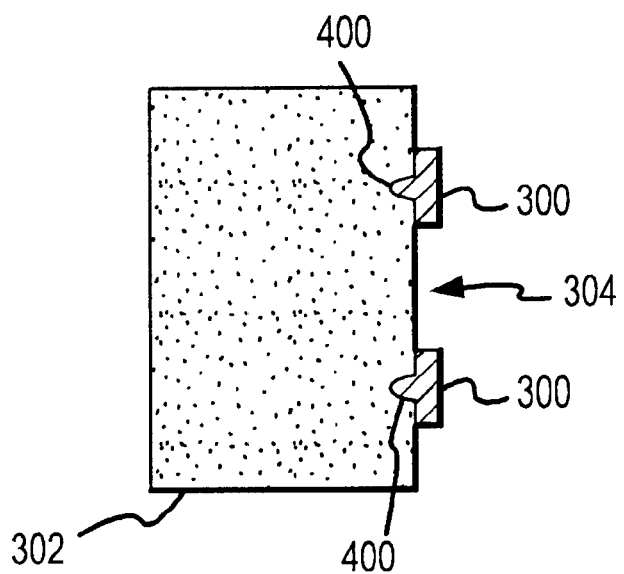
FIG. 4 shows a cross-section of the bone graft and cervical plate of FIG. 3.

Some embodiments of the present invention are described with reference to FIGS. 3 to 9. In particular, FIGS. 3 and 4 show a cervical plate 300 and bone graft 302. Cervical plate 300 has a viewing window 304, screw holes 306, and an attachment mechanism 400 (shown in phantom in FIG. 3). As best seen in FIG. 4, cervical plate 300 has attachment mechanism 400 attaching the bone graft 302 to the cervical plate 300.

Attachment mechanism 400 can be any of a number of different attachment mechanisms. For example, as shown in FIG. 4, attachment mechanism 400 comprises a pin or stud attached to the cervical plate inserted into a hole or detent in the bone graft 302. Alternatively, attachment mechanism 400 could be a spike inserted into bone graft 302 without bone graft 302 having a corresponding hole or detent to receive the spike, similar to a thumbtack. Alternatively, attachment mechanism 400 could comprise a pin or stud attached to the bone graft 302 inserted into a hole or detent in cervical plate 300. Also, attachment mechanism 400 could be any style snap lock or friction fitting, such as the cavity formed in FIG. 5 between protrusions 504, explained in more detail below. Moreover, while two attachment mechanisms 400 are shown, more or less attachment mechanisms could be used. Further, attachment mechanism 400 could be an adhesive layer between the cervical plate 300 and bone graft 302. Still further, attachment mechanism 400 could be a screw device so that bone graft 302 and cervical plate 300 are attached using a screw mechanism. Finally, the cervical plates 300 could be made integral to the bone graft 302, although that would be difficult due to the numerous sizes and shapes of bone grafts and plates necessary to perform the surgery.

Figure 5:
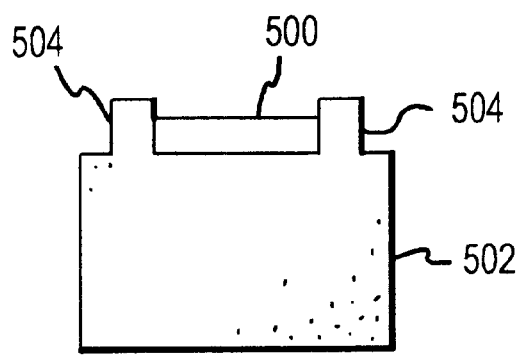
FIG. 5 shows an alternative attachment mechanism illustrative of the present invention.

FIG. 5 shows cervical plate 500 attached to a bone graft 502 by prongs 504 on bone graft 502. As shown, prongs 504 attached to the bone graft grasp cervical plate 500 forming a frictional engagement. Alternatively, but not shown, cervical plate 500 could have prongs that grasp bone graft 502.

As one of ordinary skill in the art would recognize on reading this disclosure, the number of ways the bone grafts could be attached to the cervical plate is numerous. To the extent alternative attachment means are not expressly identify above, this description should not be limited to the embodiments identified and described above. Rather, the specific embodiments identified are for illustrative purposes.

Figure 6:
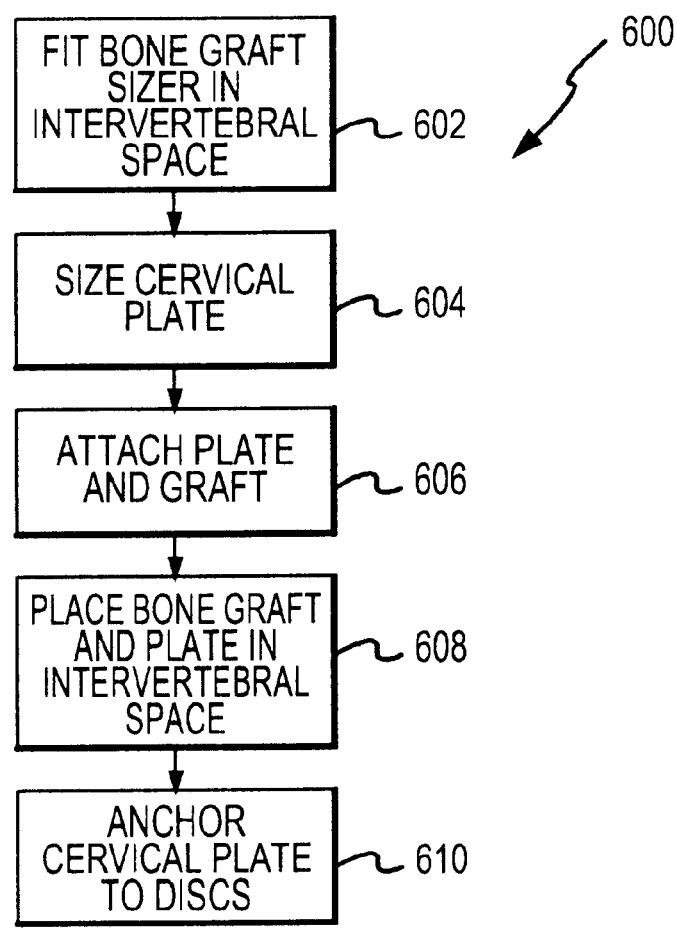
FIG. 6 is a flowchart 600 illustrating use of the present invention.

FIG. 6 is a flowchart 600 illustrating a method of using the present invention. In particular, the surgeon fits a bone graft sizer into the intervertebral space to size the bone graft, step 602. Then, the appropriate sized intervertebral graft is secured and the surgeon sizes a cervical plate based on the size of the graft and the length of the overall construct, step 604. Once the cervical plate and bone graft are sized, the surgeon attaches the bone graft and the cervical plate, step 606. Next, the bone graft and plate device is placed in the intervertebral space such that the adjacent vertebral endplates hold the bone graft and plate in place, step 608. The cervical plate is then anchored to the adjacent vertebral bodies, step 610. Because the surgeon attached the cervical plate to the bone graft, and the adjacent vertebrae hold the bone graft in place, the cervical plate remains fixed in place while the surgeon anchors the plate to the vertebrae.

As one of ordinary skill in the art would recognize on reading the above disclosure, the same general device and procedure can be used when inserting multiple bone grafts. For example, if fusing four vertebrae, a surgeon would need to place three bone grafts. Conventionally, three bone grafts are sized and placed in the intervertebral space and a cervical plate is sized for the construct. Using the present invention, one intervertebral space at the top, bottom, or middle is left devoid of a bone graft. The intervertebral space is sized with a bone graft sizer. The appropriate sized graft would then be secured. A cervical plate measured to fit the three level construct would then be secured and the sized bone graft would be attached to the cervical plate. The one bone graft with the cervical plate attached is fitted into the patient. The one bone graft attached to the cervical plate provides stability to the cervical plate and proper orientation of the screw holes to the adjacent vertebral body to facilitate attachment of the cervical plate to the vertebrae.

Alternatively, two or more bone grafts could be sized using sizers and attached to the cervical plate prior to insertion of the grafts in the intervertebral space. While this alternative method is possible, it is believed to be more difficult due to surgical space constraints.

As mentioned above, conventionally inserting the bone graft and cervical plate includes using a retracting device to hold the adjacent discs apart, inserting the bone grafts, removing the retracting device, allowing the adjacent discs to squeeze the bone grafts, then placing and anchoring the cervical plate. A difficulty arises using the present invention because the conventional retracting devices need to be removed prior to placing and anchoring the combined bone graft and cervical plate. On removing the retracting devices, the adjacent discs move together making it difficult to insert the bone graft between the adjacent discs.

Figure 7A:
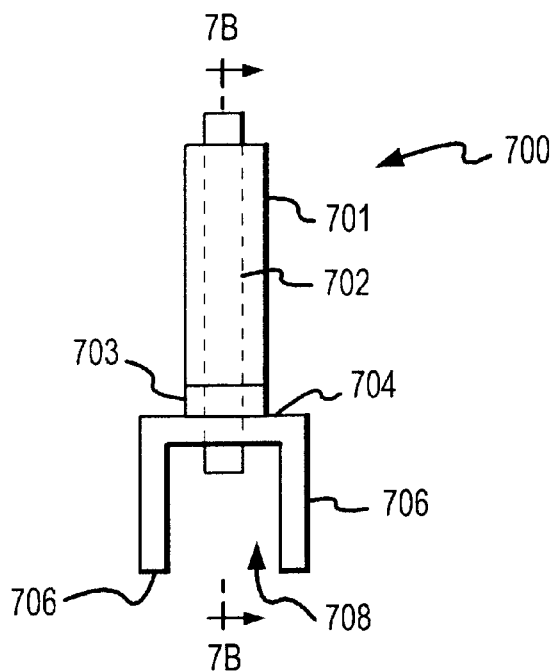
FIGS. 7A and 7B show an impactor illustrative of the present invention.

FIG. 7A shows an impactor 700 capable of opening the space between the discs to ease the insertion of the bone graft attached to the cervical plate. Impactor 700 has a handle 702 and a cervical plate holder 704. A distracter 701 and a collar 703 fits over handle 702 such that cervical plate holder 704 extends just below collar 703. Extending from collar 703 are prongs 706 forming cavity 708. Impactor 700 could have various numbers of prongs, but it is believed two prongs work well. Cervical plate holder 704 is designed to hold the cervical plate such that the prongs 706 extend downward beyond the cervical plate and bone graft attachment. The cervical plate holder 704 could be attached to the cervical plate by, for example, a pin and detent, a spike, an adhesive, a friction coupling, a snap lock, etc. Prongs 706 could be spaced to form cavity 708 such that placing the cervical plate in the cavity 708 would form a friction fitting releasably coupling the cervical plate to the impactor 700. However, because the bone graft is often wider than the cervical plate, and depending on whether the prongs function as a scissor like assembly or a wedge like assembly, it is likely the cavity formed by the prongs would not be a sufficient attachment mechanism.

Figure 7B:
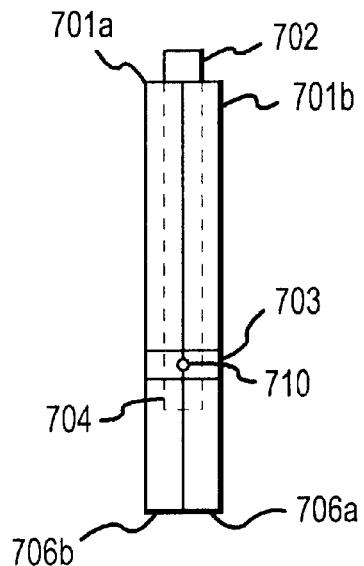

Impactor 700 could function as either a scissor like assembly or a wedge like assembly. FIG. 7B shows impactor 700 assuming a scissor like assembly. As shown handle 702 extends internal to distracter 701. Distracter 701 is formed by two distracter handles 701a and 701b attached to a pivot 710 on collar 703. Each prong 706 also is formed by two blades 706a and 706b attached to the pivot 710. Separating distracters 701a and 701b would cause blades 706a and 706b to move apart also. Thus, in operation, blades 706a and 706b would be inserted between two adjacent vertebrae. Distracter handles 701a and 701b would be moved apart causing the blades to move apart and open the intervertebral space. To ease insertion of the blades between adjacent vertebrae, the blades should be as thin as possible, but thick enough to withstand the force necessary to separate the vertebrae without fracture. Further, is would be possible to jog the blades 706a and 706b off the centerline so that the blades would be at a slight angle. For example, if blades 706a and 706b were angled to the left (top) to right (bottom) and a jog (not shown) connected the blades 706a and 706b to the pivot 710. In this case, the angle of the blades would make it easier for the surgeon to insert the blades between the vertebrae. In this case, it would be preferable if the jog and blades formed an acute angle.

Impactor 700 is shown with handle 702 and distracter handles 701a and 701b. This is because in operation, the distracter is placed with the graft residing above the intervertebral space. The blades 706a and 706b and distracter handles 701a and 701b are inserted between adjacent vertebrae. The distrater handles 701a and 701b are separated causing blades 706a and 706b to separate and open the intervertebral space. With the space open, handle 702 having the cervical plate and bone graft attached to cervical plate holder 704 is lowered relative to the distracter and blades until the bone graft and plate are placed. The distracter handles are closed causing the vertebrae to close and squeeze the bone graft. While other design possibilities are within the spirit and scope of the present invention, it is believed relative movement between the handle and distracter handles/blades is the easiest to implement in surgery.

As an alternative to the blade method above, the prongs 706 could be wedge shaped. In this case, the distracter 701, collar 703 and pivot 710 could be removed from the mechanism. The prongs 706 would then start at a point at the end and angle outward and upward towards the handle 702. The wedge would separate the adjacent discs allowing placement of the bone graft in the intervertebral space. In this case, while the wedge and bone graft could move together, it may be beneficial to include a distracter and collar so the wedge could open the space prior to insertion of the bone graft.

Figure 8:
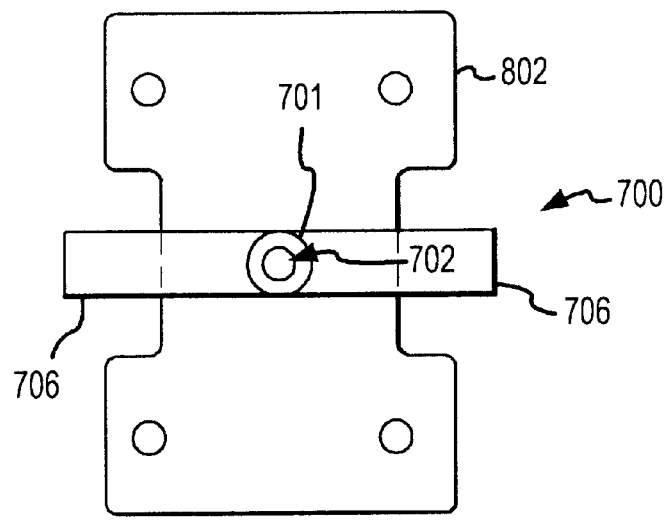
FIG. 8 shows a plan view of the impactor with a cervical plate illustrative of the present invention.

Once the bone graft is placed using either style, the impactor 700 would be completely removed from the patient. Thus, the cervical plate would be releasably coupled to the cervical plate holder of the impactor prior to insertion. FIG. 8 shows a top side elevation view of the impactor 700 holding a cervical plate 802. Cervical plate 802 is shown without a viewing window or a bone graft, but one could be used if desired. Further, FIG. 8 shows impactor 700 without the jog and using blades instead of a wedge.

Figure 9:
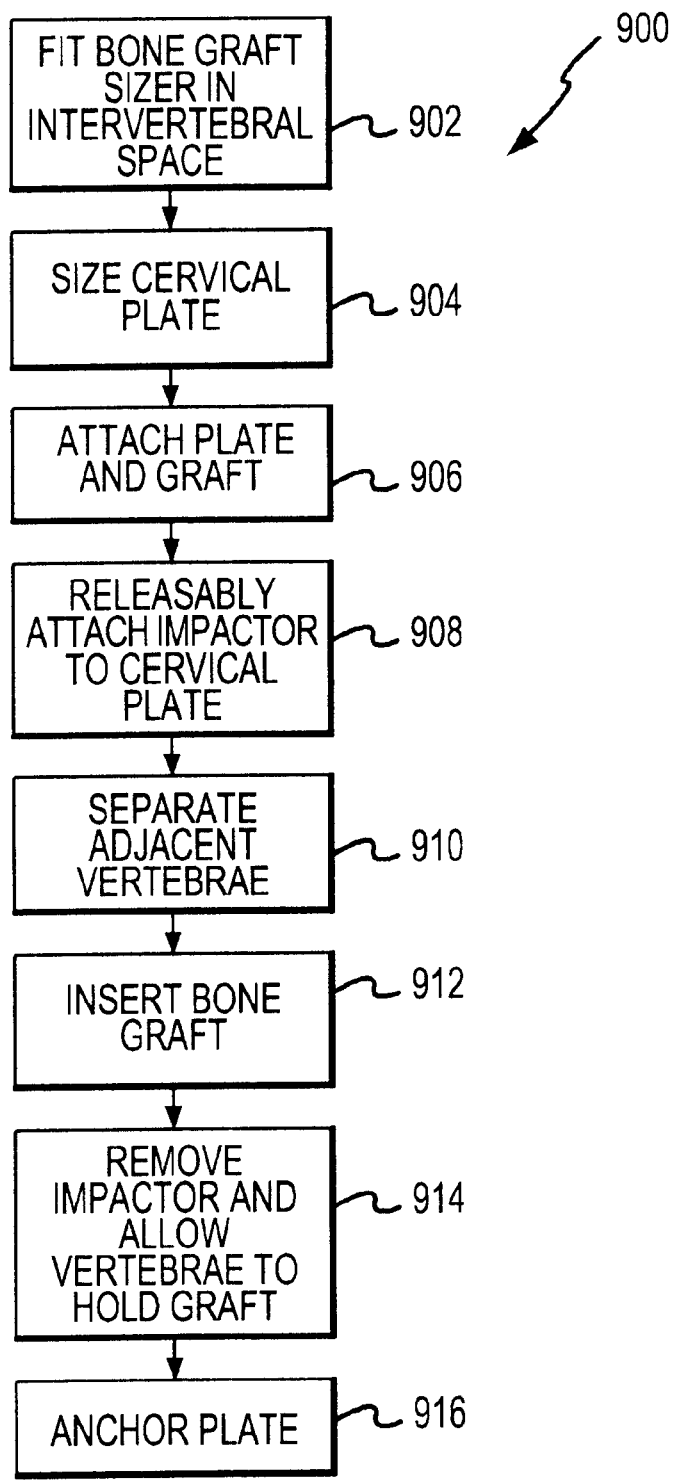
FIG. 9 is a flowchart illustrative of a use of the impactor consistent with the present invention.

FIG. 9 is a flowchart 900 illustrating using the impactor 700 with the cervical plate 802. For convenience, flowchart 900 is described for insertion of a single bone graft. One of skill in the art will recognize on reading the disclosure, however, that the device and procedure would be usable with insertion of multiple bone grafts. Initially, the surgeon sizes a bone graft with the bone graft sizers, step 902. For a single level fusion, once the bone graft is sized, the size of the cervical plate is automatically determined because the relationship between the end of the bone graft and the overhang on the cervical plate needed to ensure the screw holes of the cervical plate are optimally placed over the adjacent vertebral bodies is fixed, step 904. Once the cervical plate and bone graft are sized, the surgeon attaches the bone graft and the cervical plate, step 906. Next, the impactor is releasably attached to the cervical plate, step 908. The impactor with the cervical plate and bone graft is used to separate the adjacent vertebrae, step 910. With the impactor holding the adjacent vertebrae apart, the bone graft is inserted in the intervertebral space such that the screw holes of the cervical plate are placed to facilitate anchoring to the adjacent vertebrae, step 912. The impactor is removed allowing the adjacent vertebrae to hold the bone graft and cervical plate in place, step 914. Finally, the cervical plate is anchored to the vertebrae, step 916.

While the invention has been particularly shown and described with reference to some embodiment thereof, it will be understood by those skilled in the art that various other changes in the form and details may be made without departing from the spirit and scope of the invention.

I claim:

1. An apparatus useful in placing bone grafts in a spine of a patient, comprising:

a cervical plate;

the cervical plate having a top side and a bottom side;

at least one attachment mechanism;

the cervical plate adapted to be attached to at least one vertebrae; and the attachment mechanism directly coupling at least a first bone graft to the bottom side of the cervical plate prior to insertion of at least the first bone graft into an intervertebral space, such that prior to attaching the cervical plate to the at least one vertebrae, the cervical plate is held in place by adjacent vertebrae squeezing the first bone graft.

2. The apparatus according to claim 1, wherein the at least one attachment mechanism comprises at least one protrusion.

3. The apparatus according to claim 2, wherein the at least one protrusion is a spike.

4. The apparatus according to claim 1, wherein the at least one attachment mechanism comprises at least one corresponding detent adapted to receive the at least one protrusion.

5. The apparatus according to claim 1, wherein the at least one attachment mechanism comprises at least one of a screw, an adhesive, a nail, and a plurality of prongs.

6. The apparatus according to claim 1, further comprising an impactor, the impactor comprising a handle, a cervical plate holder releasably coupled to the cervical plate, and at least one impactor prong;

the handle extending above the cervical plate holder and the at least one impactor prong extending below the cervical plate holder, such that the at least one impactor prong is adapted to separate the adjacent vertebrae to allow insertion of at least the first bone graft into the intervertebral space.

7. The apparatus of claim 6, wherein the at least one impactor prong comprises at least two impactor prongs.

8. The apparatus of claim 6, wherein the at least one impactor prong is wedge shaped.

9. The apparatus of claim 6, wherein the impactor comprises a collar;

a pivot;

the pivot is attached to the collar;

at least one distracter handle;

at least one blade;

the at least one distracter handle attached to the pivot and extending above the cervical plate holder;

the at least one impactor prong comprises at least one blade attached to the pivot; and the at least one blade adapted to fit between adjacent vertebrae so that operation of the at least one distracter handle causes the at least one blade to separate the adjacent vertebrae.

10. The apparatus of claim 9, wherein the at least one distracter handle comprises at least two distracter handles and the at least one blade comprises at least two blades such that moving the at least two distracter handles apart causes the at least two blades to move apart.

11. The apparatus of claim 10 wherein the at least two blades are perpendicular to the cervical plate.

12. The apparatus of claim 11 wherein the at least two blades form an angle with the cervical plate.

13. The apparatus of claim 6, wherein the impactor is releasably coupled to the cervical plate by at least one of a screw, a nail, a pin, a detent, an adhesive, a friction fitting, and a snap lock.

14. The apparatus of claim 13, wherein the impactor is releasably coupled to the top side of the cervical plate.

15. An apparatus useful in placing bone grafts in a spine of a patient, comprising:

a cervical plate;

the cervical plate having a top side and a bottom side;

at least one attachment mechanism;

at least one bone graft coupled to the cervical plate by the at least one attachment mechanism;

the at least one bone graft sized to fit into at least one intervertebral space; and the at least one bone graft coupled to the cervical plate prior to insertion of the at least one bone graft into the at least one intervertebral space such when the at least one bone graft is inserted into the at least one intervertebral space, the cervical plate is positioned such that it can be attached to at least one vertebrae.

16. The apparatus according to claim 15, wherein the attachment mechanism comprises:

at least one pin attached to the bottom of the cervical plate, and at least one detent attached to the at least one bone graft, such that the at least one detent and the at least one pin form a fitting.

17. The apparatus according to claim 15, wherein the attachment mechanism comprises:

at least one detent attached to the bottom of the cervical plate; and at least one pin attached to the at least one bone graft, such that the at least one detent and the at least one pin form a fitting.

18. The apparatus according to claim 15, wherein the attachment mechanism comprises at least one of a screw, a nail, a plurality of prongs, and an adhesive.

19. The apparatus according to claim 15, wherein the cervical plate is adapted to be attached to the at least one vertebrae using at least one screw and the cervical plate is positioned for optical placement of the at least one screw.

20. An apparatus for use in replacing vertebral discs in a spine of a patient, comprising a cervical plate adapted to be attached to at least two vertebrae separated by at least one intervertebral space;

at least one bone graft adapted to be inserted into the at least one intervertebral space;

first means for attaching; and the first means for attaching attaches the at least one bone graft to the cervical plate prior to insertion of the at least one bone graft into the at least one intervertebral space;

such that the at least one bone graft can be placed in the at least one intervertebral space and the cervical plate will be arranged and held by the bone graft in the intervertebral space so the cervical plate can be attached to the at least two adjacent vertebrae.

21. The apparatus according to claim 20, wherein the first means for attaching is at least one protrusion on the cervical plate and a corresponding at least one detent on the bone graft.

22. The apparatus according to claim 20, wherein the first means for attaching is a pair of prongs extending from the bone graft to grip the cervical plate.

23. The apparatus according to claim 20, wherein the first means for attaching comprises at least one of a screw, an adhesive, a nail, and a plurality of prongs.

24. The apparatus according to claim 20, further comprising:

an impactor; and the impactor comprises second means for attaching;

the second means for attaching releasably attaches the impactor to the cervical plate.

25. The apparatus according to claim 24, wherein the impactor comprises at least one handle and means for separating adjacent vertebrae to allow for insertion of a bone graft into a space between the adjacent vertebrae.

26. The apparatus according to claim 24, wherein the second means for attaching comprises at least one of a pin, a detent, a screw, and an adhesive.

27. The apparatus according to claim 25, wherein the means for separating is at least one impactor prong.

28. The apparatus according to claim 25, wherein the means for separating comprises at least one blade.

29. The apparatus according to claim 25, wherein the means for separating comprises at least one wedge.

30. A system for inserting at least one bone graft in an intervertebral space, comprising:

a cervical plate;

the cervical plate having a top side and a bottom side;

at least one bone graft sized to be inserted in at least one intervertebral space between adjacent vertebrae;

an impactor for separating the adjacent vertebrae to allow the at least one bone graft to be inserted in the at least one intervertebral space;

at least a first attachment mechanism that couples the at least one bone graft to the cervical plate; and at least a second attachment mechanism that releasably couples the impactor to the cervical plate, such that the impactor separates the adjacent vertebrae so the at least one bone graft coupled to the cervical plate can be inserted into the at least one intervertebral space and the impactor removed from the cervical plate causing the adjacent vertebrae to hold the bone graft such that the cervical plate is placed in position to be attached to the adjacent vertebrae.

31. The system according to claim 30, wherein the at least a first attachment mechanism and the at least a second attachment mechanism are different.

32. The system according to claim 30, wherein the placement of the cervical plate for attachment to the adjacent vertebrae is optimal.

33. A method for inserting a bone graft into an intervertebral space with a cervical plate attached to the bone graft, comprising the steps of:

sizing an intervertebral space to identify an appropriate bone graft;

selecting an appropriate cervical plate based on the sized intervertebral space and adjacent vertebrae;

attaching the appropriate bone graft to the appropriate cervical plate;

placing the appropriate bone graft in the intervertebral space with the appropriate cervical plate attached and positioned to be anchored to the adjacent vertebrae;

allowing the vertebrae to hold the appropriate bone graft in place; and anchoring the appropriate cervical plate to the adjacent vertebrae.

34. The method according to claim 33, wherein the sizing step includes using sizers.

35. The method according to claim 33, further comprising the step of attaching an impactor to the appropriate cervical plate.

36. The method according to claim 33, further comprising the step of separating the adjacent vertebrae to allow placement of the appropriate bone graft in the intervertebral space.

37. The method according to claim 35, further comprising the step of removing the impactor.

38. A method for inserting a bone graft into an intervertebral space with a cervical plate attached to the bone graft, comprising the steps of:

placing at least a first bone graft in at least a first intervertebral space;

sizing at least a second intervertebral space to identify an appropriate second bone graft capable of fitting in the second intervertebral space;

selecting a cervical plate based on the adjacent vertebrae surrounding the at least a first intervertebral space and the second intervertebral space;

attaching the appropriate second bone graft to the cervical plate selected in the selecting step;

placing the appropriate second bone graft in the second intervertebral space with the cervical plate selected in the selecting step attached and positioned to be anchored to the adjacent vertebrae spanning at least the appropriate second bone graft and the first bone graft;

allowing vertebrae to hold the identified second bone graft in place; and anchoring the selected cervical plate to the vertebrae.

39. The method according to claim 38, wherein the sizing step includes the using sizers.

40. The method according to claim 38, further comprising the step of attaching an impactor to the cervical plate selected in the selecting step.

41. The method according to claim 38, further comprising the step of separating adjacent vertebrae to allow placement of the appropriate second bone graft in the second intervertebral space.

42. The method according to claim 40, further comprising the step of removing the impactor.

* * * * *